United States Patent
Planckaert

(10) Patent No.: US 11,785,950 B2
(45) Date of Patent: Oct. 17, 2023

(54) USE OF DRIED CHICORY ROOT TO PROTECT POULTRY AND LIVESTOCK AGAINST ECTOPARASITES OR AS INSECT REPELLANT

(71) Applicant: Cosucra Groupe Warcoing S.A., Warcoing (BE)

(72) Inventor: Philippe Planckaert, Rollegem (BE)

(73) Assignee: Cosucra Groupe Warcoing S.A., Warcoing (BE)

( * ) Notice: Subject to any disclaimer, the term of this patent is extended or adjusted under 35 U.S.C. 154(b) by 0 days.

(21) Appl. No.: 17/830,567

(22) Filed: Jun. 2, 2022

(65) Prior Publication Data
US 2022/0287313 A1 Sep. 15, 2022

Related U.S. Application Data

(63) Continuation of application No. 16/641,299, filed as application No. PCT/EP2018/074538 on Sep. 12, 2018, now abandoned.

(30) Foreign Application Priority Data

Sep. 12, 2017 (EP) .................................. 17190677
Mar. 30, 2018 (BE) .................................. 2018/5217

(51) Int. Cl.
*A61K 36/00* (2006.01)
*A01N 65/12* (2009.01)

(52) U.S. Cl.
CPC .................................. *A01N 65/12* (2013.01)

(58) Field of Classification Search
CPC .................................. A61P 33/00; A61P 33/14
See application file for complete search history.

(56) References Cited

U.S. PATENT DOCUMENTS

| 2004/0001898 A1 | 1/2004 | Malnoe et al. |
| 2012/0329756 A1 | 12/2012 | Courtois et al. |
| 2016/0095337 A1* | 4/2016 | Peet .................. A21D 2/366 426/549 |
| 2017/0188590 A1 | 7/2017 | Peet et al. |
| 2018/0177201 A1 | 6/2018 | Peet et al. |

FOREIGN PATENT DOCUMENTS

| CN | 107114776 A | * | 9/2017 | |
| GB | 2362574 A | | 11/2001 | |
| WO | WO-0226242 A2 | * | 4/2002 | ............ A23L 33/22 |
| WO | 2015/195928 A1 | | 12/2015 | |
| WO | 2016057382 A1 | | 4/2016 | |

OTHER PUBLICATIONS

International Search Report and Written Opinion dated Dec. 20, 2018 in International Application No. PCT/EP2018/074538.
Bischoff TA et al., "Antimalarial Activity of Lactucin and Lactucopicrin: Sesquiterpene Lactones Isolated from *Cichorium intybus* L.," Journal of Ethnopharmacology, vol. 95, Nos. 2-3, 2004, pp. 455-457 (available online Sep. 11, 2004).
Foster JG et al., "In Vitro Analysis of the Anthelmintic Activity of Forage Chicory (*Cichorium intybus* L.) Sesquiterpene Lactones Against a Predominantly Haemonchus contortus Egg Population," Veterinary Parasitology, vol. 180, Nos. 3-4, 2011, pp. 298-306.
Hoste H et al., "The Effects of Tannin-Rich Plants on Parasitic Nematodes in Ruminants," Trends in Parasitology, vol. 22, No. 6, Jun. 2006, pp. 253-261 (available online Apr. 24, 2006).
Jensen AN et al., "The Effect of a Diet with Fructan-Rich Chicory Roots on Intestinal Helminths and Microbiota with Special Focus on Bifidobacteria and Campylobacter in Piglets Around Weaning," Animal, vol. 5, No. 6, 2011, pp. 851-860 (available online Jan. 4, 2011).
Thamsborg SM et al., "Alternative Approaches to Control of Parasites in Livestock: Nordic and Baltic Perspectives," Acta Veterinaria Scandinavica, vol. 52 (Supplement 1), No. S27, 2010, pp. S27-S31.
European Patent Office "Opinion," issued in European Patent Application No. 17 190 677.9, dated Jun. 22. 2018, 4 pages.
European Patent Office, "European Search Report," issued in European Patent Application No. 17 190 677.9 dated Jun. 22, 2018, 3 pages.

* cited by examiner

*Primary Examiner* — Qiuwen Mi
(74) *Attorney, Agent, or Firm* — Amster, Rothstein & Ebenstein LLP

(57) ABSTRACT

The invention is situated in the field of animal feed supplements, more particularly in the field of feed supplements for diminishing ectoparasitic infestation of animals. The invention provides the use of such a feed supplement in farming of livestock and poultry. The invention also provides for a process of manufacturing such a feed supplement.

16 Claims, No Drawings

USE OF DRIED CHICORY ROOT TO PROTECT POULTRY AND LIVESTOCK AGAINST ECTOPARASITES OR AS INSECT REPELLANT

CROSS-REFERENCE TO RELATED APPLICATIONS

This application is a continuation of U.S. patent application Ser. No. 16/641,299, filed Feb. 24, 2020, which is a U.S. national stage entry under 35 U.S.C. § 371 of PCT International Patent Application No. PCT/EP2018/074538, filed Sep. 12, 2018, which claims priority to Belgian Patent Application No. 2018/5217, filed Mar. 30, 2018, and European Patent Application No. 17190677.9, filed Sep. 12, 2017, the contents of each of which are incorporated herein by reference in their entirety.

FIELD OF THE INVENTION

The invention is situated in the field of animal feed supplements, more particularly in the field of feed supplements for diminishing ectoparasitic infestation of animals. The invention provides the use of such a feed supplement in farming of livestock and poultry. The invention also provides for a process of manufacturing such a feed supplement.

BACKGROUND OF THE INVENTION

Farming of livestock and poultry often requires animals to be residing in close proximity to each other, especially in cold environments. This makes them prone to spreading of infections with ectoparasites such as mites, stinging insects and the like.

Since meat of livestock and poultry is usually meant for human consumption, the regulations regarding the use of pest and disease controlling agents are very strict to avoid contamination of the food chain with such agents. Yet, farmhouses or barns need to be cleaned or made free from ectoparasites regularly in order to avoid poor life conditions for the animals as well as disease spreading.

Poultry are for example regularly infected by mites, which causes stress, reduction of egg laying performance and higher mortality.

Livestock can be prone to both external and internal parasite infestations with mites, lice, flies, fleas, roundworms, tapeworms, flukes etc. Mange (or scabies) for example in livestock is a skin condition caused by microscopic mites in or on the skin. The mites cause intense itching and discomfort which is associated with decreased feed intake and production. Scratching and rubbing results in extensive damage to hide and fleece and potential wound infections.

Cattle are regularly infested with mites (acariosis) especially during winter periods when animals are housed in intensive way and when hygienic conditions are not optimal (presence of humid hear coat is favourable to the development of mites.).

The most common species of mites present on cattle are scaroptes, chorioptes and psoroptes ovis. A female mite is laying 1 to 3 eggs a day, and lasts about 50 days. The mites' faeces cause allergic reactions of the host's coat, which reacts by producing exudations, skin thickening, scales and crusts. The mites suck the exudates and secretions of the skin. Lesions are mostly starting at the tail head, and around the neck, and spread to the rest of the body. The animals suffer from severe itching and react by scratching, biting and rubbing against objects. The injuries caused infections which lead to weight loss and reduced milk production. Approx. 85% of the blue white Belgian bovines suffer from mites, and the disease is also a pest for other species in rather humid and cold regions specifically during winter (Canada, USA, rest of Europe), or on camelids during rainy seasons.

Also, snails (escargots) are suffering from acariasis as the major infection source. The preferential habitat of snails are humid conditions. This is also the most convenient environment for acariasis.

There are no vaccines or pour-on treatment that will protect cattle by making them immune to the mites.

There is hence a constant need for new approaches in controlling pests or ectoparasites in livestock and poultry farms without posing risks to the food chain.

SUMMARY OF THE INVENTION

Chicory root, is known as a prebiotic and has been used as an animal feed supplement for reducing internal parasite infestation of worms, and for regulating food transit. It is the merit of the applicant of having discovered that dried chicory root can surprisingly, advantageously, be used for decreasing ectoparasitic infestation in livestock and poultry.

Disclosed herein is a composition comprising dried chicory root, produced by a 2-step process of drying the raw chicory root and processing it in flakes of roughly 5 cm to 15 mm, preferably 3 cm to 15 mm, such as between 2 cm and 15 mm, re-drying said flakes and optionally grinding into small particles of approximately 0.1 to 2 mm, preferably between 0.5 to 1.5 mm, preferably of about 1 mm. The final dried chicory root product has a dry matter content of 88% w/w or more, preferably of 89% w/w or more, more preferably of 90% w/w or more, corresponding to a moisture content of between about 8 and 12% w/w, preferably of between 9 and 11% w/w. The composition disclosed herein is a natural composition, which has substantially not been treated chemically. Said dried chicory root composition comprises inulin, sesquiterpene lactone and chicory root pulp fraction.

Hereto, the present invention is in particular captured by any one or any combination of one or more of the below numbered statements:

1. A composition comprising dried chicory root for use in reducing, treating or preventing ectoparasitic infestation of livestock or poultry or as an insect repellent, wherein between 0.1 and 5% of dried chicory root is added to the animal feed, preferably between 0.1 and 1%, such as between 0.1 and 0.5%, for poultry and between 0.5 and 5% for livestock such as between 0.5 and 3%. Particular examples of ectoparasites are ticks (suck blood), lice & mites (don't suck blood). Preferred examples of insects on which the composition can have a repellent effect are biting insects (hematophagous, i.e. they suck blood), black flies, horse flies, gnats, fleas, horn flies, midges, mosquitoes, face flies, stable flies, tsetse flies, etc.. Alternatively, a sesquiterpene lactone extract or concentrate obtained from chicory roots is provided, for use as a feed supplement for use in reducing, treating or preventing ectoparasitic infestation of livestock or poultry or for use as an insect repellent.

2. The composition, extract or concentrate for use according to statement 1, which is administered to poultry, more particularly to laying poultry.

3. The composition, extract or concentrate for use according to statement 1 or 2, for use in reducing, treating or preventing the presence of red mites in poultry.

4. The composition, extract or concentrate according to statement 3, which additionally promotes the decrease of broken eggs, the improvement of egg laying cycle, and decreases the mortality of poultry, decreased feather pecking, and decreases or avoids infestation with worms.

5. The composition, extract or concentrate for use according to statement 1, which is administered to livestock.

6. The composition, extract or concentrate for use according to statement 5, for use in reducing, treating or preventing the presence of infestation with mites in livestock.

7. The composition, extract or concentrate for use according to statement 5, for use as an insect repellent in livestock.

8. The composition according to any one of statements 1 to 7, comprising inulin, sesquiterpene lactone and pulp fraction.

9. The composition for use according to any one of statements 1 to 8, comprising at least 50 wt. % of inulin, preferably more than 60 wt. % of inulin.

10. The composition for use according to any one of statements 1 to 9, wherein said inulin has an average degree of polymerization by number of at least 3.

11. The composition, extract or concentrate for use according to any one of statements 1 to 10, wherein the species of chicory is Cichorium intybus L.

12. The composition, extract or concentrate for use according to any one of statements 1 to 11, wherein said sequiterpen lactones are selected from lactucine, dihydrolactucine, lactucopicrine and dihydrolactucopicrine.

13. The composition for use according to any one of statements 1 to 12, wherein said pulp fraction comprises soluble and insoluble fibers.

14. The composition for use according to any one of statements 1 to 13, wherein said pulp fraction comprises cellulose.

15. The composition for use according to any one of statements 1 to 14, having a dry matter content of 88% w/w or more, preferably of 89% w/w or more, more preferably of 90% w/w or more. This is corresponding to a moisture content of between about 8 and 12% w/w, preferably of between 9 and 11% w/w.

16. The composition for use according to any one of statements 1 to 15, comprising or consisting essentially of particles having an average diameter of less than 2 mm, preferably approximately 0.1 to 2 mm, preferably between about 0.5 to 1.5 mm, more preferably of about 1 mm; or comprising dried chicory root flakes or shreds, preferably having an average size of between 3 cm and 15 mm, preferably between 2 cm and 15 mm.

17. The composition for use according to any one of statements 1 to 16, which consists essentially of a natural product. Indeed, the composition disclosed herein has been processed physically only, i.e. by washing with water, drying, grinding, optionally followed by a second drying step and fine grinding or milling into small particles of average particle size as depicted herein. The raw chicory root material has not been subjected to chemical treatment with solvents or extraction means etc. in order to reach the dried chicory root composition.

18. The composition for use according to any one of statements 1 to 17, further comprising from 0.5 to 1.5 wt. % calcium stearate to further avoid water absorption resulting into clumping.

19. Use of a composition comprising dried chicory root, or sesquiterpene lactone extract or concentrate obtained from chicory roots as a feed additive in the production of a feed product or a feed supplement for treating, reducing, or preventing ectoparasitic infestation of livestock or poultry, wherein said feed product comprises between 0.1 and 5% by weight of said dried chicory root feed supplement, preferably between 0.1 and 1% for poultry, between 1 and 5% for pigs, horses, or domestic animals and between 0.2 and 5%, between 0.5 and 3%, or between 0.2 and 1.5% for livestock. Particular examples of ectoparasites are ticks (suck blood), lice & mites (don't suck blood). Preferred examples of insects on which the composition can have a repellent effect are biting insects (hematophagous, i.e. they suck blood), black flies, horse flies, gnats, fleas, horn flies, midges, mosquitoes, face flies, stable flies, tsetse flies, etc.

Typically, sheep and cattle would receive a dosage of between 0.2 and 1.5%, preferably between 0.3 and 1% of the dried chicory root composition mixed into the normal feed.

Pigs, piglets, horses and dogs or similar domestic animals typically would receive a dosage of between 0.1 and 10% of the dried chicory root composition mixed into the normal feed. Indicative dosages are: 0.3% to 3%, preferably of about 1 to 1.5% in feed for sows and piglets and about 0.3 to 1% in feed for fattening pigs during the duration of the stay. Said amount can be increased to between 5 to 10% in the last week of fattening of boars to reduce scatole compounds and boar taint. In pet food for e.g. cats and dogs, a dosage of between about 0.3 and 1.2% of the dried chicory root composition mixed into the normal feed.

Poultry and birds in general would typically receive a dosage of between 0.1 and 1%, preferably between 0.1 and 0.6% of their normal feed. Indicative dosages are: 0.2% in poultry feed especially during the first 3 weeks of fattening; 0.1 to 0.5% in feed for laying hens.

20. Use according to statement 19, wherein the chicory root or sesquiterpene extract or concentrate from chicory root is fed to the animal daily. The period of use can be during the majority of the breeding or production period in order to have a protective effect. For example in ruminants, a period of up to 10 weeks, such as up to 8 weeks or up to 6 weeks could be envisaged in order to avoid re-infestation. For poultry for example, the treatment could be maintained throughout the whole lauing period e.g. for laying hens and the like, ue to the beneficial effects on animal health and laying performance.

21. Use according to statement 19 or 20, wherein the chicory root or sesquiterpene extract or concentrate from chicory root is fed to the animal daily for a period of up to 6 weeks, for example for about 5 to 20 days, more preferably for between 10 and 18 days.

22. A method of producing a composition comprising dried chicory root comprising the following steps: a) washing of the raw chicory root material;

b) cutting the raw material into flakes, preferably having a size of between about 3 cm to 15 mm, more preferably of between about 2 cm to about 15 mm; and c) drying the fresh chicory root flakes by direct or indirect heating.

23. The method according to statement 22, additionally comprising the steps of:

d) grinding, crushing or milling the dried flakes obtained in step c) into a fine powder having an average particle diameter of less than 2 mm, preferably of between 0.6 and 1.2 mm, more preferably between 0.8 and 1 mm; and e) additional drying the milled dried chicory root obtained in step d); and f) optionally adding a silicate or calcium stearate to avoid water absorption.

24. The method according to statement 17, wherein when the chicory root is dried by direct or indirect heating, the temperature of heating is performed at a temperature of between 50 and 80° C., preferably between 60 and 70° C. Said drying step is typically done for at least 30 minutes.

25. The method according to any one of statements 22 to 24, wherein when the chicory root is dried by direct heating, the temperature of said heating is at least of 100° C. for at least 1 second.

26. A dried chicory root composition comprising at least 50%, preferably at least 60% of inulin comprising between 0.3 and 0.5% by weight of sesquiterpene lactone and comprising a pulp fraction, or a sesquiterpene lactone extract or concentrate obtained from chicory roots.

27. The composition, concentrate or extract according to statement 26, wherein said sesquiterpene lactones are preferably selected from: lactucine, dihydrolactucine, lactucopicrine and dihydrolactucopicrine.

28. The composition according to any one of statements 26 to 27, wherein said dried chicory root composition has a dry matter content of at least 85% by weight, preferably at least 90% by weight.

29. The composition according to any one of statements 26 to 28, wherein the water activity of the composition is comprised between 0.3 and 0.5.

30. The composition according to any one of statements 26 to 29, obtained by the method of any one of statements 26 to 29.

31. Alternatively, in all the above statements, the chicory root composition could be replaced by chicory leaf or leaves. Such leaves can be provided as a feed supplement for use reducing, treating or preventing ectoparasitic infestation of livestock or poultry or as an insect repellent. Such leaves can be fed actively by adding them to the feed or can be seeded or planted on the field or pastures of grazing animals, leading to feeding of grazers of leaves and grass in the pasture.

32 Alternatively, in all the above statements, sesquiterpene lactone extract or concentrate obtained from chicory roots can be used.

DETAILED DESCRIPTION

Before the present method of the invention is described, it is to be understood that this invention is not limited to particular methods, components, products or combinations described, as such methods, components, products and combinations may, of course, vary. It is also to be understood that the terminology used herein is not intended to be limiting, since the scope of the present invention will be limited only by the appended claims.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. It will be appreciated that the terms "comprising", "comprises" and "comprised of" as used herein comprise the terms "consisting of", "consists" and "consists of", as well as the terms "consisting essentially of", "consists essentially" and "consists essentially of".

The recitation of numerical ranges by endpoints includes all numbers and fractions subsumed within the respective ranges, as well as the recited endpoints.

The term "about" or "approximately" as used herein when referring to a measurable value such as a parameter, an amount, a temporal duration, and the like, is meant to encompass variations of +/−20% or less, preferably +/−10% or less, more preferably +/−5% or less, and still more preferably +/−1% or less of and from the specified value, insofar such variations are appropriate to perform in the disclosed invention. It is to be understood that the value to which the modifier "about" or "approximately" refers is itself also specifically, and preferably, disclosed.

Whereas the terms "one or more" or "at least one", such as one or more or at least one member(s) of a group of members, is clear per se, by means of further exemplification, the term encompasses inter alia a reference to any one of said members, or to any two or more of said members, such as, e.g., any ≥3, ≥4, ≥5, ≥6 or ≥7 etc. of said members, and up to all said members.

All references cited in the present specification are hereby incorporated by reference in their entirety. In particular, the teachings of all references herein specifically referred to are incorporated by reference.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination.

In the following detailed description of the invention, reference is made to the accompanying drawings that form a part hereof, and in which are shown by way of illustration only of specific embodiments in which the invention may be practiced. It is to be understood that other embodiments may be utilized and structural or logical changes may be made without departing from the scope of the present invention. The following detailed description, therefore, is not to be taken in a limiting sense, and the scope of the present invention is defined by the appended claims.

The term "ectoparasites" intends to include all infesting parasites that live on the outside of the host, either on the skin or the outgrowths of the skin of poultry, domestic animals and livestock. Some non-limiting examples of ectoparasites of cattle are ticks (suck blood), lice & mites (don't suck blood) such as: Amblyomma ticks, Boophilus cattle ticks, Dermacentor ticks, Haemaphysalis ticks, Hyalomma ticks, Ixodes ticks, Rhipicephalus ticks, and cattle mites such as scab and mange mites, cattle mange, Psoroptes, Sarcoptes, Chorioptes, or Demodex causing acariosis or acariasis.

Some non-limiting examples of ectoparasites of poultry are: bloodsucking poultry mites of which the most important species are: Dermanyssus gallinae (red fowl mite, red poultry mite, roost mite, chicken mite), Ornithonyssus sylviarum (northern fowl mite), and Ornithonyssus bursa (tropical fowl mite); non-bloodsucking poultry mites of which the most relevant species are Cnemidocoptes gallinae (depluming mite or itch mite), Cnemidocoptes mutans (scaly leg mite), Epidermoptes bilobatus (scaly skin mite)

Some non-limiting examples of ectoparasites of horses and equids in general are Chorioptes equi (itchy leg mite), Demodex equi (the horse follicle mite, leading to demodectic mange), Psoroptes equi (scab mite or equine body mite, leading to prosoptic mange), Sarcoptes scabiei var. equi (common mange mite, leading to sarcoptic mange).

Some non-limiting examples of ectoparasites of sheep and ovines in general are: Chorioptes ovis (chorioptic mange mite), Psorergates ovis (sheep itch mite), Psoroptes ovis (sheep scab mite, Sarcoptes scabiei var. ovis (itch mite, or sarcoptic mange mite).

Some non-limiting examples of ectoparasites of pigs are: Demodex phylloides (pig follicle mite) and Sarcoptes scabiei var. suis (pig itch mite or sarcoptic mange).

Some non-limiting examples of ectoparasites of cattle and bovines in general are: Demodex bovis (cattle follicle mite), Chorioptes bovis (chorioptic mange mite), Psoroptes ovis (cattle scab mite), Sarcoptes scabiei var. bovis (cattle itch mite, or sarcoptic mange mite).

Some non-limiting examples of ectoparasites of pet animals such as cats and dogs are: Demodex canis (canine follicular mange mite, or red mange mite), Demodex cati (feline follicular mange mite), Otodectes cynotis (ear mite), Notoedres cati (feline scabies, or cat mange mite), Cheyletiella spp., (walking dandruff), Pneumonyssoides caninum (nasal mite), Sarcoptes scabiei var. canis (canine scabies).

The term "insect" when used in combination with the use of the dried chicory root composition as insect repellent is intended to encompass all biting insects which feed on blood of livestock such as horses, equids, cattle including ovines, bovines, camelids, ruminants, domestic animals etc. Some non-limiting examples of such insects are: biting insects (hematophagous, i.e. they suck blood), black flies, horse flies, gnats, fleas, horn flies, midges, mosquitoes, stable flies, face flies, tsetse flies, etc.

The term "livestock" as used herein is intended to encompass domesticated animals raised in an agricultural setting to produce commodities such as food, fiber, and labor. The term includes mammalian ruminants such as bovines (cattle, bisons, buffalos, yaks and the like), ovines (goats, sheep, etc.), pigs, peccaries, camelids, alpacas, deer, elands, elks, moose, donkeys, mules, horses, Guinee pigs, rabbits, etc..

The term "pets" includes small domesticated furry animals such as guinea pigs, cavia's, dogs, cats, rabbits, and the like.

The term "poultry" as used herein includes all domesticated birds kept by humans for e.g. eggs, meat or feathers and include fowl, more specifically galliforms such as but not limited to chicken, duck, goose, quail, emu, peafowl, ostrich, pigeon, pheasant, turkey, etc..

The term "treating or preventing" when used in relation to ectoparasite infestation intends to encompass any improvement of the condition of the animal, i.e. any decrease of the infestation with the ectoparasite, preferentially mitigating said infestation and preventing re-occurrence of the infestation thereby seriously improving the animal health and well-being. Prevention of infestation as a whole is also included in the term and encompasses the avoidance of any substantial infestation with the ectoparasites in animals that had not been previously infested therewith.

The term "repellent" as used herein refers to biting insect repellent characteristics and is intended to encompass any decrease in biting incidents in livestock or poultry with biting insects as indicated herein. Ideally, no or substantially no insect biting incidents occur in the livestock or poultry, thereby seriously improving the animal health and well-being.

The term "chicory root" as used herein refers to the root of chicory, in a preferred example, the species of chicory is Cichorium intybus L species. Chicory root comprises two main components, inulin and pulp. The raw chicory root comprises about 20-25% of dry matter, which contains between 16-17% inulin. When dried up to a dry matter content of around 90%, this results in an inulin concentration in the dried chicory root composition of above 60%, typically of about 65%. Said inulin has an average degree of polymerization by number of at least 3. Additional components of the chicory root composition are sesquiterpene lactones such as the ones selected from: lactucine, dihydrolactucine, lactucopicrine and dihydrolactucopicrine. Typically, in a concentration of around 0.4 wt. %. The pulp fraction comprises soluble and insoluble fibers and cellulose.

Also the leafs of the chicory plant can be interesting, since they also contain about 0.25 wt. % on dry matter of sesquiterpen lactones. The leafs could be directly fed to grazing cattle such as cows, sheep, goats, horses, camelids etc..

Dried chicory roots comprise inulin, sesquiterpenes lactone and a pulp fraction. As used herein, the term "inulin" refers to a mixture of oligo- and/or polysaccharides of fructose which may have a terminal glucose. Inulins belong to a class of fibers known as fructans. In an embodiment, inulin can be represented, depending from the terminal carbohydrate unit, by the general formulae GFn and/or Fm, wherein G represents a glucose unit, F represents a fructose unit, n is an integer representing the number of fructose units linked to the terminal glucose unit, and m is an integer representing the number of fructose units linked to each other in the carbohydrate chain, preferably wherein n is at least 2, and m is at least 2. Inulins for use in the present invention encompass inulins with a terminal glucose which are also referred as alpha-D-glucopyranosyl-[beta-D-fructofuranosyl](n−1)-D-fructofuranosides, as well as inulins without glucose which are also referred as beta-D-fructopyranosyl-[D-fructofuranosyl](n−1)-D-fructofuranosides. Inulins for use in the present invention can also encompass branched inulin. Inulins for use in the present invention can also encompass the hydrolysis products of inulins such as fructo-oligosaccharides (FOS), also called oligofructoses, which are fructose oligomers with a DP of ≤20, and they can also encompass fructo-oligosaccharides ending with a terminal glucose with a DP of 3-5 synthesized from sucrose. Preferably said fructo-oligosaccharides have an average DP by number of at least 3 and at most 7. Suitable saccharide chains of inulin from plant origin for use in the invention can have a DP ranging from 2 to about 100. Inulin can be a liquid or a powder product.

As used herein, the terms "degree of polymerization" or "(DP)" relates to the number of monosaccharide residues present in an oligo- or polysaccharide. Often also the parameter average degree of polymerization is used. The degree of polymerization is a measure of molecular weight (MW). The DP can be calculated as the ratio of the total MW of the polymer or oligomer and the MW of the repeating units.

The average degree of polymerization (av DP) of a (polydispersed) oligo- or polysaccharide mixture is the mean of the degree of polymerization (DP) of all the molecules present in this saccharide mixture. The average degree of polymerization herein, unless otherwise specified, is calculated based on the number of molecules for each DP: av DPn or average degree of polymerization by number as described herein below.

Determination of the molecular mass distribution of the fructan sample is done by High Performance Anion Exchange Chromatography coupled with Pulse Amperometric Detection (HPAEC-PAD) on a Thermo scientific—Dionex ICS 5000 chromatographic system. Separation of the various chain lengths is achieved by a Carbopac PA100 4 mm*250 mm (+guard) at 40° C. with a flow rate of 1 ml/min. Sodium hydroxide 160 mM is used as eluent. A gradient of sodium acetate during the run allows to separate the various chain lengths. Fructan mixture standards at different concentrations are injected in order to draw the calibration curves and to assign the peaks in the chromatogram based on the retention time of the standard. The calibration curves allow determining the concentration of each molecular species in the sample.

From the obtained concentration distribution, the average polymerization degree in number $\overline{Dp_n}$ is calculated as $$\overline{Dp_n} = \frac{\sum_i N_i Dp_i}{\sum_i N_i}$$

Where Ni is the number of molecules having i residue and Dpi the number of residue.

In an embodiment, the fructan as described herein, preferably inulin, has an average DP by number of at least 3. In an embodiment, the fructan as described herein, preferably inulin, has an average DP by number of at most 500. In an embodiment, said fructan, preferably inulin, has an average DP by number of at least 3, for example of at least 5, for example of at least 7, for example at least 10, for example at least 15, for example at least 20, for example at least 25, for example at least 70. In an embodiment, the fructan as described herein, preferably inulin, has an average DP by number of at least 3 and of at most 500, preferably of at least 3 and at most 100, more preferably of at least 3 and of at most 30. In a further preferred embodiment, the fructan as described herein, preferably inulin, comprises or consists of fructooligosaccharides (FOS). In a further preferred embodiment, the fructan as described herein has an average DP by number of at least 3 and at most 20, preferably of at least 3 and at most 15, such as of at least 3 and at most 10. In yet another preferred embodiment, the fructan as described herein, preferably inulin, comprises or consists of hydrolyzed or partially hydrolyzed fructan, preferably inulin. Hydrolyzed fructan, such as hydrolyzed inulin, may for instance be obtained enzymatically (e.g. by inulinases) or may alternatively be obtained by acid and/or thermal hydrolysis.

As used herein, the term "sesquiterpene lactones" refers to a class of chemical compounds, called sesquiterpenoids (built from three isoprene units) and contain a lactone ring. Sesquiterpene lactone are comprising at least artemisinin, Lactucin, desoxylactucin, lactucopicrin, lactucin-15-oxalate, lactucopicrin-15-oxalate.

As used herein, the term "pulp fraction" refers to the pulp fraction comprised in the chicory root. It is mainly composing of soluble and insoluble fibres with a high-water retention capacity.

For use in the present invention, the chicory root is dried and ground into flakes of between 1 and 10 mm or into a fine powder having a mean particle diameter of less than 2 mm, preferably of between 0.6 and 1.2 mm, preferably of between 0.8 and 1 mm, between 0.1 to 2 mm, between about 0.5 to 1.5 mm, more preferably of about 1 mm. The mean particle size can be measured by any known technique such as sieving with a mesh having known sizes of openings and typically will be represented by any one of D10 (=arithmetic or number mean), D32 (=volume/surface mean (also called the Sauter mean)), or D43 (=the mean diameter over volume (also called the DeBroukere mean)).

Alternatively, raw inulin can be used, i.e. the raw juices of inulin obtained after extraction of the chicory pulp. This is prepared as follows: Inulin in raw form emerges from the diffusion after separation of the pulp. Inulin in raw form is practically composed of +/−75% inulin, +/−10% reducing sugars, protein residues (3%) minerals and sesquiterpene lactones, etc. The concentration of sesquiterpene lactones may therefore be somewhat higher than for the dried chicory root composition of the invention, and therefore contains +/−0.6% sesquiterpene lactones. However, this raw inulin has sticky and hygroscopic properties and is therefore not very easy in mixing and storage.

As a further alternative, a concentrate of sesquiterpene lactones can be used, resulting from separation of the minerals and sesquiterpene lactones from the raw inulin. This is prepared as follows: After obtaining the crude inulin, it is also possible to remove the raw juice from the inulin and to obtain a substance with a considerably higher concentration of sesquiterpene lactones. This concentrate could be in the form of a liquid syrup and would be particularly interesting as an ingredient for lick buckets (in the form of blocks of minerals with anti-fly/anti-mosquito and deworming effect.

As yet a further alternative, chicory seeds can be added in pastures, leading to feeding of cattle etc. of leaves and grass in the pasture.

Preparation

Further disclosed is a method of producing a composition comprising dried chicory root comprising the following steps:

a) washing of the raw chicory root material with water;

b) cutting the raw material into flakes of about 1-15 mm with any suitable means, such as slicer; and c) drying the fresh chicory root flakes by direct or indirect heating by any suitable means, such as by means of heated air. It is preferred to keep the temperature of the drying process below 80° C., in order to avoid break-down of the product. For example, the heating can be performed at a temperature of between 50 and 80° C., preferably between 60 and 70° C. Said drying step is typically done for at least 30 minutes, such as about 1 or 1.5 hours.

Said flakes can additionally be processed into a powder by:

d) grinding, crushing or milling the dried flakes obtained in step c) into a fine powder having an average particle diameter of less than 2 mm, preferably of between 0.6 and 1.2 mm, more preferably between 0.8 and 1 mm, between 0.1 to 2 mm, between about 0.5 to 1.5 mm, more preferably of about 1 mm; and e) additional drying the milled dried chicory root obtained in step d); and f) optionally adding a silicate or calcium stearate to avoid water absorption.

Said milling, grinding or crushing can be performed by any suitable means in the art such as rotor mill, ball mill, cutter mill, hammer mill or other mills and grinders or crushers known in the art.

Alternatively, the chicory root material can be dried by direct heating, wherein the temperature is at least of 100° C., such as for example 120° C. for at least 1 second, such as for example for about 0.5 or 1 minute, or more, such as for example for up to 15 minutes.

Effects

The composition comprising dried chicory root can be used for reducing, treating or preventing the presence of ectoparasites such as mites, particularly red mites in poultry, mange mites in livestock.

The effect on red mite infestation reduction in laying hens can be reasonably extrapolated to birds in general, e.g. pinguins, canaris, parrots etc.

The effects achieved by the dried chicory root composition as disclosed herein can be extrapolated to other animals than the ones tested in the disclosure, for example in but not limited to sheep, goats, pigs and game in general.

The composition comprising dried chicory root can be used for controlling scabies or mange in livestock such as in horses, ovines and bovines (specifically Belgian-Blue-White).

Although the most surprising effect found by adding the dried chicory root into animal feed was the anti-ectoparasitic and insect repellent effect, many other advantages can be obtained in terms of improvement of animal health and well-being.

The composition comprising dried chicory root can be used for decreasing the number of broken eggs and/or increasing the egg production cycle of poultry.

The composition comprising dried chicory root can be used for increasing the length of egg-laying in poultry, even more particular laying hens.

The composition comprising dried chicory root can be used for decreasing the mortality of poultry, more particularly laying poultry, even more particular laying hens.

The composition comprising dried chicory root can be used for decreasing the feather pecking of poultry.

The composition comprising dried chicory root can be used for deworming poultry or livestock or for decreasing the infestation of poultry and livestock with endoparasites such as worms such as roundworms tapeworms or flatworms.

The composition comprising dried chicory root can be used for treating or preventing malaria.

The present disclosure is further explained in the examples below, which are not to be seen as limiting the scope of protection of the invention.

EXAMPLES

Example 1: Effect of Adding Dried Chicory Root in Feed for Poultry

A comparative test was done on a farm with 50.000 laying hens. 0.4% of dried chicory root was added in the laying hens' existent feed. The feeding with this formula has started one month before the end of the egg production of the laying hens, a period where typically problems of reduced eggshell quality, increased feather picking etc.

Shell Quality

During the experiment, the number and the weight of eggs are registered daily, feed consumption is recorded monthly, and egg production, egg mass, daily feed intake and feed conversion (feed consumed per 1 g of produced egg mass) are calculated as follows: Hen-day egg production=(Average daily egg production÷Average daily number of birds alive)×100.

At 34, 46, 58 and 70 weeks, one egg from each hen is collected to determine eggshell quality indices, i.e. eggshell thickness and eggshell density. Shell thickness is measured near the equator of the egg. Eggshell density (dried shell weight per unit of shell area, $mc/cm^2$) is calculated by Eggware software. Egg shell breaking strength, using an Instron Testing machine, is measured. The eggs are compressed at a constant crosshead speed of 10 mm/min, and breaking strength is determined at the moment of the eggshell fracture.

Mortality Rate

Mortality rate is usually expressed in percentages using the following equation: Mortality rate=(no. of dead birds÷total no. of birds)×100

Measurement of Feather Pecking

Gentle feather pecking (GFP) Hen uses beak to gently peck at feathers of conspecific. This pecking is normally ignored by the recipient and usually does not result in the removal of a feather. Usually occurs in bouts where the hens will GFP several times in a single bout. Normally directed at the back or tail, but may be directed at the head. Count total number of pecks Severe feather pecking (SFP) Hen uses beak to forcefully peck at victim. Victim will usually respond to pecking by moving away or retaliating. May result in removal of a feather. Usually occurs as a single event, but may happen twice in a row. Will not occur in bouts. Usually directed toward the back, rump, or tail, but may be directed at the head. Count total number of pecks Aggressive pecking (AP) Occurs when one hen raises her head and forcefully stabs beak either once or multiple times at another hen. Aggressive pecks will usually be directed at the head, but may also be directed at the body. The recipient will usually show avoidance behaviour by ducking or moving away from aggressive bird. May be associated with a chase, standoff, or leap. Count total number of pecks Enrichment pecking (EP) Hen uses beak to peck at top or sides of hay bale or plastic box (HAY and BOX rooms only). Count total number of pecks

Red Mites Measurement

Since the majority of the population of mites is in the environment rather than on the hens, monitoring the number of mites in the hen house, on feeder tracks, in nest boxes, cracks, crevices etc. is a good measure of the amount of mites present. The number of mites per $m^2$ is measured in the hen house before the presence of laying hens and before the cleaning of the hen house after the hens have left. Although the. Typically, laying hens will be kept in the hen house for about 18 months.

Deworming Activity Measurement

One way of establishing worm presence or number is to actually count the worms in the dropping of the hens. Other signs of worm infestation are: mucky bottoms; dishevelled, depressed appearance; weight loss; drop in egg production; pale comb etc..

Results

The eggs produced before the administration of chicory root in the formula were considered of poor quality and the proportion of broken eggs was increasing.

After 3 to 4 days of inclusion of 0.4% of chicory root to the formula, eggshell quality was improving significantly and egg shells were shinier and more colourful. Less egg losses occurred though breaking. Also, the mortality rate of the laying hens which is normally quite high at this time in the production cycle, was significantly reduced.

After 14 days, the inclusion of chicory root in the formula has been stopped, and egg shell quality decreased again within the first following days, clearly linking the effect to the dried chicory root.

During the period of the 0.4% chicory root inclusion feather pecking was also significantly reduced and feathers were growing again.

Completely unexpected, when cleaning the hen house after the hens were removed, the farmer remarked that he was not bitten once by mites. Upon investigating in more detail, the bodies of hens were not infected by red mites. The presence of red mites in the hen house was practically nihil, which had never been the case before the use of the dried chicory root.

At the arrival of pullets in the rearing house, diarrhoea is occurring regularly because of stress, change of feed, and risk of fat liver syndrome (typical of pullets just before laying eggs with rather excessive feeding). Adding the dried chicory root composition at 0.4% in the feed formula seemed sufficient to improve quality of faeces, even after only 2 to 3 days of feeding.

Next, a sensory evaluation of eggs from hens fed with and without dried chicory root composition was performed in order to ensure no taste issues occurred in the resulting eggs.

60 eggs of each group (Diet with and without 0.4% dried chicory root composition) have been collected after four weeks of trial. The eggs were evaluated by triangle test. Each panellist received three half hard boiled eggs: two from one diet and one from the other diet. The panellist was asked to identify the unique sample. Six possible order combinations had been used. The panellist was instructed to taste first the white, then the yolk. Panellists were asked which criteria permitted to find a difference. 50 eggs of each set have been boiled for 12 minutes and peeled off. To avoid panellists to be influence by colour differences, the light was filtered with red filter in the laboratory.

Results 32 panellists participated to the triangle test. Among them, 14 panellists (<50%) identified correctly the unique sample. Panellists comments are listed in Table 1 below. For a significant difference, at least 16 panellists should have the correct answer (at risk α=0.05%).

Conclusion: There is no significant difference between samples B1 and B2. Incorporation of dried chicory root composition at 4 kg/ton in hens' diet does not detectably impact sensory quality of eggs. Indeed, when looking at the comments of the pannelists in Table 1 below, there is not a single criterion that is unique for the 2 groups of eggs.

TABLE 1

| Panellists comments | |
| --- | --- |
| Sample B1 | Sample B2 |
| White taste stronger | No taste difference, white less hard, yolk slightly different |
| Yolk harder and different | |
| More taste (Better) | Taste stronger and yolk more smooth |
| Yolk more yellow and smooth, same taste | No difference for white, more taste for yolk (saltier) |
| Yolk smaller and less dry (no difference for white) | More taste for the yolk |
| White less hard | More smooth and bitter taste |
| White smoother, no taste difference | |

Example 2: Effect of Adding Dried Chicory Root to Horse Feed

Tests based on an amount of 75 g/day of dried chicory root composition (roughly about 0.5 to 1.5% on the feed) during 10 days were found to be sufficient for having a repulsive effect on horse-flies. Horses that showed an important number of stings of horse flies before the treatment were no longer stung after the treatment, showing a clear repulsive effect.

In addition, and unexpectedly, the skin of the horses treated with the dried chicory root recovered rapidly from dermatitis caused by stinging or infestation with mites. Without wanting to be bound to any theory, the bitter substance in the dried chicory root likely changes the composition of the sweat and/or blood of the animal, and consequently gives a repelling effect to the insects that feed on the blood of the horse. Sesquiterpene lactones also have anti-inflammatory and antimicrobial properties, which may in part explain the speed with which healing of wounds and dermatitis is observed.

Example 3: Effect of Adding Dried Chicory Root to Cattle Feed

To test the effect on cattle, 150 g of dried chicory root composition was administered to 8 Belgian white-blue cows that were infested with psoroptes and chorioptic mites. After 6 days of application, the first signs of control over the infested wounds were identified and no further growth of the mites occurred.

When the dosage was reduced to 80 g/day during 1 week, the effect was lost. Re-applying a dosage of between 150 and 200 g/day restored the control after 5 to 6 days. Said amount corresponds to roughly 1 to 2% of dried chicory root on the total feed.

Example 4: Trail with Dried Chicory Root Composition in Feed of 10 'Belgian Blue White' Heifers Infected with Scabies All heifers received a daily dosage of 150 g dried chicory root composition per animal during 6 weeks. The heifers were identified with a badge number fixed on the ear. The heifers were kept free on straw in 2 boxes pro 5.

Aim of the Trial

The main aim was to evaluate the effect of dried chicory root on the reduction of skin lesions due to the presence of scabies. This was done by dosing 150 g/heifer/day of dried chicory root composition in the feed for 6 weeks. Said amount corresponds to roughly 1 to 2% of dried chicory root on the total feed.

The observation was done at the start, during the 6 weeks of administration and after a period of 35 days post administration. The post administration period is used to observe the resistance to or recurrence of scabies after the 6 weeks of administration period.

In addition, the health status was checked by considering feed ingestion, growth and effects on the newborn calves.

Visual Observations Regarding Scabies Reduction

During and after the treatment, the skin of the heifers was clearing and became more shining. No "wet" places were detected (during and after the period of administration).

In addition, the injuries (lesions) on the skin were quite nicely reduced or healed, with only some small spots of darker hear being visible on 1 or 2 heifers after treatment.

No Tactic (Amitraz) or other known anti-scabies treatment compositions were used during and after the period of administration of the dried chicory root composition, The young cows (after calving) behaved normal on grass during the summer, and no scabies re-appeared. After 35 days post administration.

Other Health Benefits Observed

In addition to the effect on scabies, feed ingestion of forage and dry feed seemed improved. The heifers behaved well and the calving period (May/June) occurred correctly. The newborn calves were also more healthy in general. The breeder mentioned that in general 40% of newborn calves of his cows need to be fed by a drink probe (tube), while the calves of the 10 heifers receiving the dried choicory root composition that wer calving during the same period, accepted the milk from the heifers easily from the 1st day (no need to probe feed them).

Conclusion: This limited trial shows the beneficial effects of adding dried chicory root composition to the feed of young cows (heifers) on the reduction of scabies lesions and the prevention of re-infection post treatment.

Example 5: Comparative Test of Dried Chicory Root Composition and Amitraz on Infestation with Mites and Lice and on Development of Scabies In this trial, the efficacy of dried chicory root composition as a nutritional strategy to treat scabies (in this study dom-inantly caused by the mite Chorioptes bovis) and lice infections was compared against a control treatment with local application of Amitraz (Tactic®; commonly used for scabies treatment on Belgian farms).

The whole trial lasted for 15 weeks and was subdivided in 2 periods: a pre-treatment period of 9 weeks, a treatment period of 3 weeks, and a 3 week post-treatment period.

The trial started with pre-treatment period of 9 weeks during which the animals were housed in a straw-bedded free stall and received no preventive treatment against scabies and lice. At the end of the pre-treatment period, the degree of scabies lesions (clinical index) and counts of mites and lice in skin-scraping samples were evaluated.

Animals

Twenty Belgian Blue cattle (6 heifers and 14 cows) were used in this trial. Cattle with mild or severe visual signs of scabies infection were selected, tied, shaved, scored for scabies lesions (clinical index) and skin scraping samples were taken for counts of mites and lice. Next, the animals were divided into 2 groups, a control group and a treatment group, based on the results of the clinical index and mite—lice counts at the end of the pre-treatment phase. At the start of the treatment period, animals were housed in a tie-stable, shaved and tied to prevent physical contact with other animals.

Control group: The animals in the positive control group were treated according to the standard ILVO (Flecmish Institute for Agriculture and Fishery) scabies prevention protocol which consisted of treatment with Amitraz (Tactic) and removal of the crusts, followed by a second treatment with interval of 10 days between both treatments. After the second treatment crusts were not removed.

Treatment group: The animals in the treatment group were not treated with Amitraz (Tactic), but were fed the indicative daily dose of 200 g of dried chicory root composition per animal per day. Said amount corresponds to roughly 1 to 2% of dried chicory root on the total feed. Dried chicory root composition was provided mixed through the daily dose of soybean meal and concentrate. The nutritional treatment with dried chicory root composition lasted for 3 consecutive weeks during which the animals receive their daily dose of dried chicory root composition. In order to avoid bias due to crust removal, crusts were also removed at start of the treatment phase.

Diet

Throughout the whole trial, the animals were fed a constant diet. The roughage mixture was fed ad libitum and consisted of 40% maize silage, 40% pre-wilted grass silage and 20% straw on a dry matter (DM) basis. In addition, each animal received a fixed daily amount of 250 g soybean meal and 250 g of a vitamin-mineral concentrate.

Soybean meal and concentrates were fed in the morning before provision of the roughages. The treatment group was fed its daily dose of dried chicory root composition mixed with the soybean meal and concen-trate. The animal caretaker checked if the animals had completely finished the dried chicory root composition before providing the roughage mix.

Clinical Index

In the last week of the pre-treatment period (week 0) and every following week till the end of the post-treatment period, the clinical index was determined as a measure for scabies lesions. Per animal, the number, size and type of scabies lesions was determined using a scoring form.

A distinction was made between dried, healing lesions (type 3) and wet, active lesions (type 4). The clinical index was calculated based on the total number of lesions using the formula: Area with lesions=total squares/350*100.

In addition, an alternative clinical index was calculated based on the number of active lesions: Area with lesions type 4=squares type 4/350*100.

Lice and Mite Count

In the last week of the pre-treatment period (week 0), at the end of the treatment period (week 4) and at the end of the post-treatment period (week 8) skin scraping samples were taken for counts of mites and lice.

An area of 2 cm$^2$ was shaved using a razor blade at the neck, the back and the tail of the animal (WBT sample) and at the back of the knee (hock sample). Per animal a WBT and a Hock sample was taken and stored in a plastic vial for transportation to the laboratory of Parasitology (Faculty of Veterinary Medicine, Ghent University, Belgium).

Using microscopy, the numbers of mites and lice in each sample were counted and the types of mites and lice were identified by an expert at the Laboratory of Parasitology, Ghent University, Belgium.

Statistical Analysis

Statistical analysis was done using the Linear mixed model in R taking group and week as fixed effects and cow as a random effect. Effects are considered as significant when $P \leq 0.05$, and trends are identified at the level $0.05 < P \leq 0.10$.

In case no statistical difference between treatments was found, an equivalence test was performed calculating the 95% confidence interval. If the confidence interval of the dried chicory root group is contained in within the interval with endpoint defined as 1.5× the results of the Tactic group, than both treatments are seen as equivalent.

Results

Feed Intake/Growth

Individual feed intake was not registered during the trial, but animal care takers daily checked the intake of the dried chicory root feed of the treatment group during the treatment phase. In addition, the animal caretakers paid attention to signs of sickness or discomfort of the animals (abnormal feed leftovers, extreme scratching behavior, fever). During the trial, no signs of sickness were registered.

As weight loss can be a sign of discomfort due to scabies, the animals were weighed at the end of the pre-treatment phase (week 0) and after the post-treatment phase (week 7). Based on these weights, the average daily growth was calculated over the 7 week period (treatment+post-treatment). The daily growth was numerically higher but not significantly different (P=0.182) for the dried chicory root group (Table 2).

TABLE 2

Results of the live weight measurements and daily growth during the treatment and post-treatment period.

| | | | | |
|---|---|---|---|---|
| 305 | 1 | 809 | 820 | 0.183 |
| 351 | 1 | 831 | 828 | −0.050 |
| 367 | 1 | 854 | 903 | 0.817 |
| 451 | 1 | 777 | 830 | 0.883 |
| 454 | 1 | 697 | 740 | 0.717 |
| 488 | 1 | 672 | 690 | 0.300 |
| 495 | 1 | 735 | 750 | 0.250 |
| 579 | 1 | 587 | 612 | 0.417 |
| 587 | 1 | 607 | 663 | 0.933 |
| 703 | 1 | 462 | 481 | 0.317 |
| 323 | 2 | 790 | 814 | 0.400 |
| 405 | 2 | 749 | 812 | 1.050 |
| 413 | 2 | 784 | 810 | 0.433 |
| 457 | 2 | 747 | 790 | 0.717 |
| 475 | 2 | 707 | 752 | 0.750 |
| 479 | 2 | 608 | 643 | 0.583 |
| 550 | 2 | 594 | 628 | 0.567 |
| 551 | 2 | 792 | 823 | 0.517 |
| 557 | 2 | 730 | 767 | 0.617 |
| 591 | 2 | 529 | 580 | 0.850 |
| Group | 1 | 703 ± 124 | 731 ± 125 | 0.477 ± 0.337 |
| Group | 2 | 703 ± 93 | 741 ± 90 | 0.648 ± 0.198 |

Group 1: Control - Tactic; Group 2: Treatment - Dried chicory root.

Clinical Index

The clinical index was for the first time determined at the end of the pre-treatment period, followed by weekly measurements during the treatment and post-treatment period.

A distinction was made between healing lesions (type 3) and active lesions (type 4) and a clinical index was calculated based on the total number of lesions, based on type 3 lesions (data not shown) and based on type 4 lesions.

The clinical index calculated based on the total lesions increased for both groups between week 0 and week 1. This increase is due to the crust removal at start of the treatment phase. Crust removal had an impact on the size of the lesions and hence on the clinical index. During the following weeks, the clinical index based on the total number of lesions remained stable and fluctuated between 6 and 7. No statistical differences were found for treatment (P=0.229) or week effect (P=0.270).

The clinical index was numerically lower for the dried chicory root group. Based on an equivalence test, the clinical index for the Tactic group was with 95% confidence maximum 15% higher than the clinical index for the dried chicory root group. This maximal differences were smaller than the defined interval of 1.5× difference, so one can tell that both treatments were equivalent for the parameters total lesions and total clinical index (Table 3).

TABLE 3

Clinical index per animal and per week, based on the number of healing lesions (3) and based on the number of active lesions (4).

| Cow | Group | 3 | 4 | 3 | 4 | 3 | 4 | 3 | 4 | 3 | 4 |
|---|---|---|---|---|---|---|---|---|---|---|---|
| 305 | 1 | 21.7 | 0.0 | 12.6 | 2.6 | 8.0 | 0.0 | 8.9 | 0.0 | 8.3 | 0.0 |
| 351 | 1 | 2.6 | 0.6 | 4.9 | 0.6 | 5.1 | 0.0 | 6.6 | 0.0 | 6.0 | 0.0 |
| 367 | 1 | 4.3 | 0.3 | 6.3 | 0.0 | 7.7 | 0.0 | 6.6 | 0.0 | 6.3 | 0.0 |
| 451 | 1 | 8.0 | 0.0 | 8.3 | 0.6 | 7.1 | 0.0 | 6.6 | 0.0 | 8.0 | 0.0 |
| 454 | 1 | 2.9 | 0.0 | 5.1 | 0.0 | 7.1 | 0.0 | 8.0 | 0.0 | 6.3 | 0.0 |
| 488 | 1 | 2.6 | 0.0 | 4.9 | 0.0 | 6.0 | 0.0 | 5.4 | 0.0 | 6.9 | 0.0 |
| 495 | 1 | 2.3 | 0.6 | 5.7 | 0.0 | 6.0 | 0.0 | 6.3 | 0.0 | 6.9 | 0.0 |
| 579 | 1 | 0.9 | 0.9 | 5.4 | 0.3 | 5.7 | 0.0 | 5.1 | 0.0 | 6.3 | 0.0 |
| 587 | 1 | 1.0 | 0.6 | 4.0 | 0.0 | 4.9 | 0.0 | 5.4 | 0.0 | 5.7 | 0.0 |
| 703 | 1 | 1.1 | 0.6 | 5.4 | 0.0 | 6.0 | 0.0 | 4.9 | 0.0 | 6.6 | 0.0 |
| 323 | 2 | 3.7 | 0.0 | 5.7 | 0.0 | 5.1 | 0.0 | 6.0 | 0.0 | 5.4 | 0.0 |
| 405 | 2 | 4.6 | 0.3 | 10.0 | 0.0 | 6.6 | 0.0 | 6.9 | 0.0 | 7.1 | 0.0 |
| 413 | 2 | 2.0 | 1.4 | 5.1 | 0.9 | 7.4 | 0.0 | 7.4 | 0.3 | 5.7 | 0.0 |
| 457 | 2 | 6.0 | 0.0 | 8.9 | 0.0 | 6.6 | 0.0 | 8.6 | 0.0 | 7.4 | 0.0 |
| 475 | 2 | 6.3 | 0.0 | 7.1 | 0.0 | 4.9 | 0.0 | 4.9 | 0.0 | 4.3 | 0.0 |
| 479 | 2 | 3.7 | 0.0 | 5.7 | 0.3 | 8.3 | 0.6 | 6.9 | 0.0 | 6.9 | 0.6 |

TABLE 3-continued

Clinical index per animal and per week, based on the number of healing lesions (3) and based on the number of active lesions (4).

| Cow | Group | 3 | 4 | 3 | 4 | 3 | 4 | 3 | 4 | 3 | 4 |
|---|---|---|---|---|---|---|---|---|---|---|---|
| 550 | 2 | 4.3 | 0.0 | 3.4 | 0.3 | 4.9 | 0.0 | 4.0 | 0.3 | 3.4 | 0.3 |
| 551 | 2 | 2.3 | 0.6 | 5.7 | 0.0 | 6.9 | 0.0 | 6.0 | 0.0 | 5.1 | 0.9 |
| 557 | 2 | 0.6 | 0.6 | 5.1 | 0.0 | 5.7 | 0.0 | 5.1 | 0.0 | 7.1 | 0.0 |
| 591 | 2 | 2.0 | 0.9 | 4.6 | 0.9 | 6.6 | 0.3 | 4.6 | 0.9 | 4.3 | 0.3 |
| Lsmeans | 1 | 4.7 | 0.3 | 6.3 | 0.4 | 6.4 | 0.0 | 6.4 | 0.0 | 6.7 | 0.0 |
| Lsmeans | 2 | 3.5 | 0.4 | 6.1 | 0.2 | 6.3 | 0.1 | 6.0 | 0.1 | 5.7 | 0.2 |

Group 1: Control - Tactic;
Group 2: Treatment - Dried chicory root

At start of the trial (pre-treatment week 0) 11/20 animals were diagnosed with mites, and in all but one sample the mites were identified as Chorioptes bovis. Only one hock sample was positive for Psoroptes ovis, which was a surprising finding as in general scabies in Belgian Blue cattle is caused by Psoroptes ovis mites. The highest counts of mites were found in the WBT area, but the numbers were very variable and ranged between 1 and 428. Seven animals were positive for mites in the hock sample and all but one were also positive for mites in the WBT sample.

At the end of the pre-treatment period (week 0), after the treatment period (week 4) skin scraping samples were taken for counts and identification of mites and lice at the neck, back and tail area (WBT area) and at the hock.

At the start of the trial, the lice identified in the skin scraping samples were of the type Haematopinus sp., with the exception of one WTB sample that contained a minority of Damalinia sp. (2/157). One sample was negative for lice (cow 703 belonging to the Tactic group). In week 4, the counts of lice decreased significantly compared to week 0 (P=0.490) and this in both treatment groups. At the end of the treatment phase (week 4), most of the mites were gone. Six (6/20) WBT samples were positive for Chorioptes bovis (3 in the dried chicory root group and 3 in Tactic group) but with very low counts (≤6), and 2 hock samples remained positive for Chorioptes bovis (one in the dried chicory root and one in Tactic group) (Table 4).

TABLE 4

Total number of mites and lice per animal and the LSmeans per group.

| Cow | Group | Total mite | Total lice | Total mite | Total lice |
|---|---|---|---|---|---|
| 305 | 1 | 0 | 217 | 0 | 0 |
| 351 | 1 | 0 | 43 | 0 | 3 |
| 367 | 1 | 0 | 1109 | 1 | 1 |
| 451 | 1 | 4 | 206 | 0 | 0 |
| 454 | 1 | 56 | 111 | 6 | 9 |
| 488 | 1 | 0 | 356 | 0 | 1 |
| 495 | 1 | 4 | 30 | 0 | 0 |
| 579 | 1 | 0 | 38 | 19 | 0 |
| 587 | 1 | 141 | 157 | 0 | 0 |
| 703 | 1 | 49 | 0 | 0 | 0 |
| 323 | 2 | 0 | 116 | 0 | 75 |
| 405 | 2 | 19 | 44 | 0 | 0 |
| 413 | 2 | 1 | 22 | 0 | 7 |
| 457 | 2 | 6 | 237 | 1 | 77 |
| 475 | 2 | 0 | 1432 | 0 | 411 |
| 479 | 2 | 0 | 146 | 0 | 24 |
| 550 | 2 | 8 | 69 | 0 | 72 |
| 551 | 2 | 496 | 277 | 0 | 33 |
| 557 | 2 | 140 | 200 | 16 | 1 |
| 591 | 2 | 0 | 96 | 5 | 40 |
| LSmeans | 1 | 25 ± 46 | 227 ± 329 | 3 ± 6 | 1 ± 3 |
| LSmeans | 2 | 67 ± 157 | 264 ± 419 | 2 ± 5 | 74 ± 122 |

Group 1: Control - Tactic;
Group 2: Treatment - Dried chicory root

As no statistical differences were found between treatment for counts of mites (Table 4), an equivalence test was performed. In week 0, there were on average 45 mites more counted in the dried chicory root group and one can tell with 95% confidence that the difference between dried chicory root and Tactic will be lower than 4.5× the count of mites in the Tactic group. On week 4, there was no difference in mites between both groups.

Conclusions

Although this was a limited trial (both in number of animals and in time), it seems that the dried chicory root composition has a beneficial effect on the reduction of mite ans lice infestation and on the general clinical index related to scabies lesions, which is similar to that of Tactic. The preliminary results show no statistically relevant difference between the use of dried chicory root and Tactic. We note that Tactic tends to induce resistance in mites or lice, implying the need for continued administration. This effect is currently under investigation for the dried chicory root composition.

Example 6: Trial with Dried Chicory Root Composition on 80 High Yielding Dairy Cows as Fly Repellent Introduction Horn flies, stable flies and face flies can cause a lot of stress to cows, impact the productivity and cause infections on bite wounds and spread summer mastitis and analplasmosis.

The dried chicory root composition disclosed herein has been evaluated on 80 high yielding Holstein dairy cows as a repulsive towards flies.

The 80 high productive milk cows received a 200 g dried chicory root composition per day dosage during 2 weeks. The dried chicory root composition was mixed to the raw forage feed in the mixer.

The animals were severly annoyed by stable and face flies, and also some horn flies just before start of the trial. Weather conditions were about 30° C. in the afternoons of the first week.

Results

A significant drop of flies was observed from the second day, and cows were not annoyed anymore by flies during at least 3 weeks from the start of the trial.

Clear signs of cleaning of the skin were observed, indicating a better health status.

Considerations

The cows were relieved from the irritations of flies during the period of administration of dried chicory root composition and during a short period after.

Conclusion

We can conclude that dried chicory root acts as a good repulsive to ectoparasites such as horse flies, stable flies and face flies.

The invention claimed is:

1. A method for reducing or treating ectoparasitic infestation of livestock, pets or poultry or for repelling insects in livestock, pets or poultry, comprising administering a composition comprising dried chicory roots to livestock, pets or poultry, and measuring lesions, stings, or a combination thereof on the skin of livestock, pets or poultry, wherein the lesions, stings, or the combination thereof on the skin of livestock, pets or poultry is reduced compared to the lesions, stings, or the combination thereof on the skin of livestock, pets or poultry not being administered the composition comprising dried chicory roots, wherein the dried chicory roots are from *Cichorium intybus L* and contain sesquiterpene lactones selected from lactucine, dihydrolactucine, lactucopicrine and dihydrolactucopicrine, wherein the composition is added to an animal feed, and wherein between 0.1 and 5% by weight of dried chicory root is added to the animal feed.

2. The method according to claim 1, wherein the composition is administered to poultry.

3. The method according to claim 2, wherein the method is for reducing or treating the presence of red mites in poultry.

4. The method according to claim 1, wherein the composition is administered to livestock.

5. The method according to claim 4, wherein the method is for reducing or treating the presence of infestation with mites in livestock.

6. The method according to claim 4, wherein the method is for repelling insects in livestock.

7. The method according to claim 1, wherein the composition comprises:
   at least 50 wt. % of inulin;
   sesquiterpene lactones; and
   pulp fraction comprising soluble and insoluble fibers.

8. The method according to claim 1, wherein the composition has a dry matter content of 88% w/w or more.

9. The method according to claim 1, wherein the composition comprises dried chicory root particles having an average diameter of less than 2 mm; or comprises dried chicory root flakes or shreds having an average size of between 1 cm and 15 mm.

10. The method according to claim 1, wherein the composition consists essentially of a natural product, optionally further comprising from 0.5 to 1.5 wt. % calcium stearate.

11. The method according to claim 1, wherein between 0.1 and 1% by weight of dried chicory root is added to the animal feed for poultry, between 1 and 5% by weight of dried chicory root is added to the animal feed for pigs, horses, or pets, and between 0.5 and 3% by weight of dried chicory root is added to the animal feed for livestock.

12. The method according to claim 1, wherein the composition comprises more than 60 wt. % of inulin; sesquiterpene lactones; and pulp fraction comprising soluble and insoluble fibers.

13. The method according to claim 1, wherein the composition comprises more than 60 wt. % of inulin having an average degree of polymerization by number of at least 3; sesquiterpene lactones; and pulp fraction comprising soluble and insoluble fibers.

14. The method according to claim 1, wherein the composition has a dry matter content of 89% w/w or more.

15. The method according to claim 1, wherein the composition has a dry matter content of 90% w/w or more.

16. The method according to claim 1, wherein the composition comprises dried chicory root particles having an average diameter of approximately 0.1 to 2 mm.

* * * * *